United States Patent [19]

Sawayama et al.

[11] Patent Number: 5,554,792
[45] Date of Patent: Sep. 10, 1996

[54] N-VINYLFORMAMIDE COMPOSITIONS

[75] Inventors: Shigeru Sawayama, Yokohama; Kohichi Satoh, Zama, both of Japan

[73] Assignee: Mitsubishi Kasei Corporation, Tokyo, Japan

[21] Appl. No.: 421,018

[22] Filed: Apr. 13, 1995

Related U.S. Application Data

[63] Continuation of Ser. No. 115,168, Aug. 31, 1993, abandoned.

[30] Foreign Application Priority Data

Sep. 1, 1992 [JP] Japan ................................. 4-233853

[51] Int. Cl.⁶ ........................ C07C 209/90; C07C 233/01
[52] U.S. Cl. ........................................... 564/4; 564/215
[58] Field of Search .......................................... 564/4, 215

[56] References Cited

U.S. PATENT DOCUMENTS 2,430,949  11/1947  Porter et al. ................................ 564/4
2,787,634  4/1957  Coover et al. ............................... 564/4
4,359,454  12/1982  Hoffman ..................................... 424/5
4,814,505  3/1989  Kroener et al. .......................... 564/216
4,846,985  7/1989  Rizvi et al. ............................. 252/47.5

FOREIGN PATENT DOCUMENTS 61-289068  12/1986  Japan .
62-195352  8/1987  Japan .
63-190862  8/1988  Japan .
63-264559  11/1988  Japan .

OTHER PUBLICATIONS

Derwent Abstract #87-032917/05 to JP61-289068 (1987).

Primary Examiner—José G. Dees
Assistant Examiner—Mary C. Cebulak
Attorney, Agent, or Firm—David G. Conlin; Linda M. Buckley

[57] ABSTRACT

Disclosed herein is an N-vinylformamide composition comprising 250 ppm by weight or less of formic acid based on N-vinylformamide.

According to the invention, the purity and polymerizing activity of N-vinylformamide are preserved for a long time.

16 Claims, No Drawings

N-VINYLFORMAMIDE COMPOSITIONS

This is a continuation of application Ser. No. 08/115,168 filed Aug. 31, 1993 now abandoned.

BACKGROUND OF THE INVENTION

1. Field of the Invention

The present invention relates to an N-vinylformamide (hereinafter referred to as "NVF") composition. More particularly, it relates to an NVF composition having excellent stability upon storage and a method of handling NVF.

2. Prior Art

NVF may be utilized as polymerizable monomeric materials. In particular, modified polymers derived therefrom have recently been expected to be applied as cationic polymers having a vinylamine unit to dehydrating flocculants for organic sludge and paper-making reagents.

It is known, however, that NVF may often be deteriorated partially resulting in decrease of its quality during its storage, purification by distillation or polymerization reaction. Such deteriorated NVF cannot provide high viscosity polymers in a stable manner.

Several means for preserving NVF stably have been known.

Japanese Patent Application Laying-open (KOKAI) No. 63-264559 (1988) proposed to store NVF under an inert gas environment in a sealed vessel. It is disclosed that the storage stability may be further improved by diluting NVF with water 5 times the weight of NVF and adjusting the pH to 6 to 8 with an aqueous alkaline solution. This proposed method is effective to some extent but insufficient to improve the storage stability of NVF.

Japanese Patent Application Laying-open (KOKAI) No. 62-195352 (1987) proposed to adjust the pH of NVF to near neutral upon purification by distillation thereof. It is recommended to add an inorganic acid, such as sulfuric or hydrochloric acid, or an organic acid, such as acetic or formic acid when the pH is high. In the proposed method, however, the resulting product may be contaminated with acidic substances although any basic substances should be eliminated. Further, the storage stabilizing effect is not consistently provided.

Japanese Patent Application Laying-open (KOKAI) No. 61-289068 (1986) describes that among conventional stabilizers for vinylic compounds, hydroquinone, phenothiazine or phenylenediamine is insufficient to stabilize NVF during its purification by distillation or storage, but only thioureas are effective. However, the storage stability is not fully satisfactory at ordinary temperatures although the stabilization effect is excellent upon distillation of NVF at higher temperatures.

SUMMARY OF THE INVENTION

After having made great efforts to overcome the problems of the prior arts, the present inventors have found that a trace amount of formic acid, which may be produced from oxidative decomposition of NVF, is an important factor in the deterioration of quality of NVF. Thus, the present invention have been attained.

Accordingly, the present invention provides an NVF composition in which the content of formic acid is controlled to 250 ppm by weight or below based on NVF.

DESCRIPTION OF THE INVENTION

The present invention will hereinbelow be described in detail.

NVF of interest in the present invention may be prepared by any of conventional methods, which include the elimination of alcohols from N-($\alpha$-alkoxyethyl) formamides as disclosed in U.S. Pat. No. 3,914,304, the elimination of hydrogen cyanide from formylalanine nitrile as disclosed in Japanese Patent Application Laying-open (KOKAI) No. 61-134359 (1986), and the thermal decomposition of ethylenebisformamide as disclosed in U.S. Pat. Nos. 4,490,557 and 4,578,515. All these methods involve thermal decomposition at a reduced pressure and an elevated temperature higher than 100° C. to provide NVF. Generally, the decomposition mixture may be subjected to distillation to recover crude NVF with a purity of 80% by weight or more.

In addition to NVF, the crude NVF may generally contain residual starting materials and by-products, such as formamide, from the preparation process. Further, NVF may generally contain various basic impurities, such as ammonia, picolines, ethylpicolines and other unknown compounds. Although the total amount of the basic impurities is difficult to quantitatively determined, it may generally be from several tens ppm to several percents, as roughly estimated from the pH value of NVF solutions. It has been believed that such basic impurities promote the decomposition of NVF during distillation thereof, as described in Japanese Patent Application Laying-open (KOKAI) No. 63-190862. The reason that the stability of NVF was improved by adjusting the pH with sulfuric or formic acid upon purification by distillation as shown in the aforementioned Japanese Patent Application Laying-open (KOKAI) No. 62-195352, has also been believed to be that the basic impurities were neutralized with the acid to form salts and thereby inactivated. These salts could be more easily separated and removed than the free basic impurities.

According to the present inventors' study, it has been found that there is a relationship between the decrease in purity of NVF during storage and the increase of formic acid, which is a trace impurity present in NVF, and the present inventors have established the mechanism of the decrease in purity of NVF during storage, which could not fully be elucidated on the basis of the amount of basic impurities in NVF. Further, it has also been found that the generation of formic acid is promoted by oxygen present in NVF, and that if the concentration of formic acid is larger than a certain value, the cationic polymerization of NVF may more readily occur to form low molecular weight polymer of NVF, resulting in decrease in purity of NVF. When the concentration of formic acid in NVF is larger than a certain value, the storage stability of NVF is significantly reduced and the conventionally known methods for improving the storage stability of NVF are almost ineffective.

According to our finding, the content of formic acid in various grades of NVF, including those having a purity of about 80% by weight or more conventionally used as starting materials for polymerization as well as especially purified ones having a purity of about 95% by weight or more, may generally be estimated to be from 500 to 10,000 ppm by weight. It is believed that the formic acid in NVF is present mostly in the form of a free acid and in part in the form of salts thereof with the basic impurities. These formic acid or salts thereof are readily analyzed quantitatively by ion chromatography. However, no one recognized or determined formic acid as an impurity in NVF. Quite surprisingly, the present inventors have found that formic acid is an important factor affecting significantly the storage stability of NVF. This unexpectedness can also be confirmed from the fact that in the aforementioned Japanese Patent Application Laying-open (KOKAI) No. 62-195352, formic acid is added on the contrary to our finding that formic acid affects adversely the storage stability of NVF.

Accordingly, in the present invention, the content of formic acid in NVF should be maintained at 250 ppm by weight or less, preferably 200 ppm by weight or less, more preferably 150 ppm by weight or less. The "formic acid" to be treated by the invention includes both the free acid and salts thereof. If the content of formic acid in NVF is larger than 250 ppm by weight, the cationic polymerization of NVF may more readily occur to form low molecular weight polymer of NVF, resulting in decrease in purity of NVF, and it will be difficult to produce a high viscosity polymer; from such NVF. The "method of handling" according to the invention may include not only methods of storing NVF in a vessel or tank, but also methods of transporting or conveying NVF by a tank truck or drum.

In the practice of the invention, it is necessary to first prepare NVF having a formic acid content of 250 ppm by weight or less. The methods for removing formic acid to purify NVF may be illustrated below.

First, distillation may be used. It should be noted, however, that mere distillation cannot remove formic acid from NVF. For instance, crude NVF to be distilled and purified is diluted with an amount of water 5 times the weight of the crude NVF, and an alkali compound is added to the resulting mixture to adjust the pH to 6 to 8 so that the formic acid is neutralized to be fixed. If the alkali is added until the pH exceeds 8, NVF may be readily decomposed causing the decrease in recovery of NVF although it is preferable in view of fixation of formic acid. The alkali compounds to be added may include alkali or alkaline earth metal hydroxides, such as sodium, potassium and calcium hydroxides, alkaline earth metal oxides, such as calcium, magnesium and barium oxides, and alkaline earth metal carbonates, such as calcium, magnesium and barium carbonates. These may be added to NVF in the form of either powder or solution in water or methanol. After adding the alkali compound, the materials are usually mixed at 0° to 30° C. for 0.1 to 2 hours. If any insoluble materials are present in the resulting mixture, filtration should be effected prior to distillation.

After purification by distillation, a small amount of an inorganic acid may preferably be added to the distillated NVF to adjust the pH followed by additional distillation, in order to further remove a trace amount of basic impurities remaining in the distilled NVF. The inorganic acid, such as sulfuric, nitric or phosphoric acid, may usually be added as such or in the form of dilute solution thereof in water or methanol to the NVF from which formic acid has been removed out, so that the pH of the NVF diluted with an amount of water 5 times the weight of NVF is 4.5 to 8.0.

The distillation of NVF to which the alkali or acid has been added may be repeated, if desired, depending on the composition of the crude NVF to be distilled, e.g., the content of formic acid and/or basic impurities therein. Also, the order of distillation is not critical in the invention.

Alternatively, purification may be carried out with an ion exchange resin. When a weakly basic ion exchange resin is used to treat NVF, formic acid can be removed from NVF. On the other hand, a weakly acidic ion exchange resin can remove the basic impurities in NVF. This method may also be combined with the aforementioned distillation.

The thus purified NVF with a formic acid content of 250 ppm by weight or less has a good quality suitable as monomer materials for polymerization. However, when the NVF is stored under the atmosphere at room temperature, formic acid may be generated in NVF and the problem of quality may arise if the formic acid content exceeds 250 ppm by weight.

Therefore, in order to maintain the formic acid content in the NVF at 250 ppm by weight or less, the NVF may be stored under an inert gas environment in a sealed vessel at a temperature of 30° C. or lower, preferably 15° C. or lower. These lower temperatures should be held to prevent the generation of formic acid. If the temperature is higher, high boiling point substances including dimers may be increasingly generated from thermal polymerization or condensation of NVF, resulting in the reduction in purity of NVF.

It is not always practical to handle NVF in the manner as described above in view of various handling conditions of industrial large-scale production, transportation to remote places, and respective storage. In order to maintain the formic acid content at 250 ppm by weight or less, a certain antioxidant may preferably be added to the NVF to form an NVF composition.

Generally, the NVF composition contains 95% by weight or more, preferably 98% by weight or more, of NVF and may further comprise 1 to 250 ppm by weight, preferably 10 to 200 ppm by weight, of formic acid and 10 to 10,000 ppm by weight, preferably 100 to 5,000 ppm by weight, of an antioxidant, based on NVF. Further, the NVF composition usually contains trace amounts of other components, for example, the starting materials remaining therein, such as formamide and N-(α-methoxyethyl)formamide.

Generally, the better the smaller content of formic acid in the NVF composition. However, it is technically difficult to reduce the formic acid content to 10 ppm by weight or less, especially 1 ppm by weight or less. Further, it is believed that even if formic acid could be completely removed from the NVF composition, an amount as small as 1 ppm by weight of formic acid would be rapidly generated in the NVF during storage.

The antioxidant is added to prevent the generation of formic acid in NVF. As a result, the quality of NVF can be preserved if the composition is allowed to stand in the air at room temperature. If the amount of antioxidant added is smaller than 10 ppm by weight, its effect is insufficient to stabilize NVF. On the contrary, amounts larger than 10,000 ppm by weight may affect the polymerizing activity of NVF.

The antioxidants which may be used in the invention include phenolic, aromatic amine and thiourea compounds. Preferred are phenolic compounds.

The phenolic compounds may include, for example, monophenol compounds, such as 2,6-di-t-butyl-p-cresol, p-methoxyphenol, hydroquinone, butylated hydroxyanisole, 2,6-di-t-butyl-4-ethylphenol, and stearyl β-(3,5-di-t-butyl-hydroxyphenyl) propionate; bisphenol compounds, such as 2,2'-methylene-bis-(4-methyl-6-t-butylphenol), 2,2'-methylene-bis-(4-ethyl-6-t-butylphenol), 4,4'-thiobis-(3-methyl-6-t-butylphenol), and 4,4'-butylidene-bis-(3-methyl-6-t-butylphenol); and high molecular weight phenols, such as 1,1,3-tris-(2-methyl-4-hydroxy-5-t-butylphenyl)butane, 1,3,5-trismethyl-2,4,6-tris (3,5-di-t-butyl-4-hydroxybenzyl) benzene, and dl-α-tocopherol. Among these compounds, 2,6-di-t-butyl-p-cresol and dl-(α-tocopherol are especially preferred.

The aromatic amine compounds may include, for example, phenyl-α-naphthylamine, phenyl-β-naphthylamine, diphenylamine, p-phenylenediamine, N,N'-diphenyl-p-phenylenediamine, N,N'-di-β-naphthyl-p-phenylenediamine, p-hydroxydiphenylamine, p-hydroxyphenyl-β-naphthylamine, and 2,2,4-trimethyldihydroquinoline. However, NVF compositions containing the aromatic amine compounds may tend to be slightly colored during storage thereof and to provide polymers having smaller molecular weights, as compared with the aforementioned phenol compounds. Thus, the aromatic amine compound should generally be used in an amount of 10 to 1,000 ppm and preferably be removed by distillation immediately before polymerization of the NVF composition.

The thiourea compounds may include, for example, thiourea, ethylenethiourea, dimethylthiourea, diethylthiourea, and diphenylthiourea. The thiourea compounds are very effective to prevent the decrease in purity of NVF but not always sufficiently effective to prevent the generation of formic acid in NVF. Therefore, these thiourea compounds may preferably be used together with the aforementioned phenol compounds.

The NVF composition comprising 1 to 250 ppm by weight of formic acid and optionally 10 to 10,000 ppm by weight of an antioxidant can be radically homo- or copolymerized in a conventional manner to provide an NVF polymer having a high viscosity in a stable manner. Any vinylic monomer can be used as a comonomer, including acrylamide, acrylic acid, acrylate esters, vinyl acetate and acrylonitrile.

An azo type polymerization initiator may be preferably used as a radical initiator for the polymerization. For example, 2,2'-azobis-(2-amidinopropane) dihydrochloride, azobis-(N,N-dimethyleneisobutylamidine) dihydrochloride, or disodium 4,4'-azobis-(4-cyanovalerate) may be used. Generally, the amount of radical polymerization initiator used is 0.005 to 5% by weight, preferably 0.05 to 0.5% by weight, based on the amount of NVF used in case of homopolymerization or the total amount of NVF and other copolymerizable monomer(s) used in case of copolymerization. The polymerization temperature may usually be chosen from the range of 30° to 100° C. depending on the molecular weight of a desired polymer.

EXAMPLES

The present invention is more fully illustrated by the following examples. However, these examples should not be construed as limiting the scope of the invention. The composition of each NVF sample was analyzed by liquid chromatography and ion chromatography.

Examples 1 to 3 and Comparative Example 1

N-(α-hydroxyethyl)formamide obtained by the reaction of acetaldehyde and formamide was methoxylated and thermally decomposed. The resulting NVF was subjected to simple distillation to give a crude NVF. The crude NVF had a purity of 83.5% by weight and contained 9.1% by weight of formamide, 7.4% by weight of N-(α-methoxyethyl)formamide and 2,500 ppm by weight of formic acid. To remove the formic acid from the crude NVF, a solution of sodium hydroxide in methanol was added so that the pH of the crude NVF diluted with water in an amount 5 times by weight that of NVF was in the range of 6 to 8. The NVF solution (600 g) was charged into a one liter pear-shape flask and subjected to distillation using a SUS rectification column with 7 theoretical plates (Sulzar Lab Packing as filler, 50 mm in outer diameter, 55 mm in height, 10 plates, distillation column of 50 mm in inner diameter and 70 mm in height). The NVF was distilled out with bath temperature of 70° to 95° C., pressure of 0.3 mmHg and reflux ratio of 1.0. Thus, purified NVF was obtained which had a purity of 99.7% by weight and contained 0.2% by weight of formamide, 0.0% by weight of N-(α-methoxyethyl)formamide and 22 ppm by weight of formic acid.

The purified NVF (29.0 g) was weighed into a 50 cc test tube and each compound as indicated in Table 1 was added so that the amount of thereof was 50, 250 or 2,000 ppm by weight.

Each test tube was placed on a vibrator and 0.2 liter per minute of air was blown thereinto from the upper inlet for 10 minutes while the liquid was mixed, so that the system was fully saturated with air. Then, the test tube was sealed. After storage at 50° C. for one week, an NVF sample was taken out and analyzed for NVF purity and formic acid content. The results are shown in Table 1. The percent reduction of purity as determined under these test conditions substantially corresponds to that at 15° C. for half a year.

TABLE 1

| | Antioxidant | | Purity | Content of Formic |
|---|---|---|---|---|
| | Name | Amount wt ppm | of NVF wt % | acid wt ppm |
| Comp. Ex. 1 | — | 0 | 95.6 | 412 |
| Ex. 1 | 2,6-di-t- | 2000 | 99.2 | 68 |
| Ex. 2 | butyl-p-cre- | 250 | 98.9 | 218 |
| Ex. 3 | sol | 50 | 96.1 | 233 |
| Ex. 4 | N,N'-diphenyl- | 2000 | 99.3 | 74 |
| Ex. 5 | p-phenylenedi- | 250 | 98.0 | 72 |
| Ex. 6 | amine | 50 | 96.2 | 165 |

Examples 7 to 9 and Comparative Example 2

Purified NVF (19.80 g, purity 99.8%, formic acid 16 ppm) obtained in a similar manner as in Example 1 was weighed into a 50 cc test tube. Further, a given amount of formic acid was added thereto so that the content of formic acid was 16, 100, 200 or 300 ppm by weight.

Each test tube was placed on a vibrator and 0.2 liter per minute of air was blown thereinto from the upper inlet for 10 minutes while the liquid was mixed, so that the system was fully saturated with air. Then, the test tube was sealed. After storage at 50° C. for one week, an NVF aliquot was used to determine the purity and the remaining sample was subjected to polymerization to prepare a water soluble polymer. The reduced viscosity of the polymer was measured. The results are shown in Table 2.

The polymerization of N-vinylformamide and the measurement of reduced viscosity were carried out in the following manner.
Polymerization:
To an aqueous solution of N-vinylformamide having a monomer concentration of 60%, 3000 ppm of 2,2'-azobisamidinopropane hydrochloride as an initiator was added based on the monomer. Suspension polymerization was effected at 70° C. in cyclohexane solvent containing 0.5% ethylcellulose as a dispersion stabilizer. The resulting polymer was immersed in acetone, dehydrated, filtered, dried under reduced pressure, and subjected to analysis for reduced viscosity.
Reduced viscosity:
From the polymer obtained in the above manner, a solution having a concentration of 0.1% was prepared with the aid of 1N aqueous sodium chloride and the reduced viscosity of the solution was measured at 25° C. in Ostwald viscometer.

TABLE 2

|  | Concentration of formic acid (wt ppm) | Purity of NVF after storage (wt %) | Reduced viscosity of polymer (dl/g) |
|---|---|---|---|
| Ex. 7 | 16 | 99.2 | 7.9 |
| Ex. 8 | 100 | 98.7 | 7.6 |
| Ex. 9 | 200 | 97.8 | 6.9 |
| Comp. Ex. 2 | 300 | 88.6 | 5.2 |

Examples 10 to 19 and Comparative Examples 3 to 6

Purified NVF (19.80 g, purity 99.8% formic acid 16 ppm) was placed into a 50 cc test tube and a given amount of formic acid and/or an antioxidant as indicated in Table 3 were added thereto. The storage test in air at 50° C. for one week was carried out as in Example 1. After storage, an NVF aliquot was used to determine the purity and the remaining sample was subjected to polymerization and the reduced viscosity of the polymer was measured, as in Example 7. The results are shown in Table 3.

Reference Examples 1 to 5

In the procedures of Example 10, purified NVF was subjected to polymerization directly or after adding thereto an antioxidant as indicated in Table 3, without subjecting to the storage test. The reduced viscosities of the resulting polymers are shown in Table 3.

TABLE 3

|  | Concentration of formic acid (wt ppm) | Antioxidant Kind | Antioxidant Amount (wt ppm) | Purity of NVF (wt %) | Reduced viscosity (dl/g) |
|---|---|---|---|---|---|
| Ex. 10 | 16 | A | 2000 | 99.1 | 8.0 |
| Ex. 11 | 100 | A | 2000 | 97.3 | 6.8 |
| Ex. 12 | 200 | A | 2000 | 96.8 | 6.6 |
| Ex. 13 | 16 | A | 250 | 98.9 | 7.8 |
| Ex. 14 | 16 | A | 50 | 96.1 | 6.4 |
| Ex. 15 | 16 | B | 2000 | 99.0 | 7.6 |
| Ex. 16 | 16 | B | 250 | 98.6 | 7.7 |
| Ex. 17 | 16 | B | 50 | 96.7 | 6.3 |
| Ex. 18 | 16 | C | 2000 | 97.6 | 4.1 |
| Ex. 19 | 16 | D | 2000 | 95.6 | 5.4 |
| Comp. Ex. 3 | 300 | A | 2000 | 81.4 | 5.0 |
| Comp. Ex. 4 | 600 | A | 2000 | 33.7 | 4.6 |
| Comp. Ex. 5 | 16 | — | 0 | 94.8 | 5.3 |
| Comp. Ex. 6 | 200 | — | 0 | 89.0 | 4.1 |
| Ref. Ex. 1 | 16 | — | 0 | 99.8 | 8.2 |
| Ref. Ex. 2 | 16 | A | 2000 | 99.5 | 8.0 |
| Ref. Ex. 3 | 16 | B | 2000 | 99.5 | 8.1 |
| Ref. Ex. 4 | 16 | C | 2000 | 99.5 | 4.2 |
| Ref. Ex. 5 | 16 | D | 2000 | 99.5 | 8.1 |

A: 2,6-di-t-butyl-p-cresol
B: dl-α-tocopherol
C: p-phenylenediamine
D: ethylenethiourea Examples 20 and 21

Purified NVF (20.00 g, purity 99.8% formic acid 16 ppm) was weighed into a 50 cc test tube. Then, 0.2 liter per minute of nitrogen was blown thereinto from the upper inlet for 10 minutes, so that the system was fully saturated with nitrogen. Then, the test tube was sealed. A storage test was effected at a given temperature as indicated in Table 4 for 6 months. After the storage test, an NVF aliquot was used to determine the purity and the remaining sample was subjected to polymerization to prepare a water soluble polymer. The reduced viscosity of the polymer was measured. The results are shown in Table 4.

Examples 22 and 23 and Comparative Examples 7 and 8

Purified NVF (20.00 g, purity 99.8%, formic acid 16 ppm) was weighed into a 50 cc test tube. Then, 0.2 liter per minute of air was blown thereinto from the upper inlet for 10 minutes, so that the system was fully saturated with air. Then, an indicated amount of 2,6-di-t-butyl-p-cresol was added and the test tube was sealed. A storage test was effected at a given temperature as indicated in Table 4 for 6 months. After the storage test, an NVF aliquot was used to determine the purity and the remaining sample was subjected to polymerization to prepare a water soluble polymer. The reduced viscosity of the polymer was measured. The results are shown in Table 4.

TABLE 4

|  | Temperature °C. | Gas for aeration | Amount of 2,6-di-t-butyl-p-cresol (wt ppm) | Purity of NVF (wt ppm) | reduced viscosity (dl/g) |
|---|---|---|---|---|---|
| Ex. 20 | 5 | Nitrogen | 0 | 99.5 | 7.7 |
| Ex. 21 | 15 | Nitrogen | 0 | 97.6 | 7.1 |
| Ex. 22 | 5 | Air | 2000 | 99.6 | 7.9 |
| Ex. 23 | 15 | Air | 2000 | 99.3 | 7.6 |
| Comp. Ex. 7 | 5 | Air | 0 | 89.2 | 5.5 |
| Comp. Ex. 8 | 15 | Air | 0 | 85.0 | 4.8 |

According to the present invention, the increase of the amount of formic acid, which causes cationic polymerization of NVF can be prevented by controlling the amount of formic acid present in NVF to a prescribed range and preferably by adding a specified antioxidant to the NVF, when handling the NVF. Any reduction in purity and polymerizing activity of NVF during storage thereof can be effectively prevented. Accordingly, the present invention is very useful industrially.

What is claimed is:

1. An N-vinylformamide composition comprising 1 to 250 ppm by weight of formic acid based on N-vinylformamide.

2. The N-vinylformamide composition according to claim 1, wherein the content of formic acid is 1 to 200 ppm by weight.

3. The N-vinylformamide composition according to claim 1, wherein the content of formic acid is 1 to 150 ppm by weight.

4. An N-vinylformamide composition comprising 1 to 250 ppm by weight of formic acid and 10 to 10,000 ppm by weight of an antioxidant, based on N-vinylformamide.

5. The N-vinylformamide composition according to claim 4, which contains 10 to 200 ppm by weight of formic acid.

6. The N-vinylformamide composition according to claim 4, which contains 100 to 5,000 ppm by weight of an antioxidant.

7. The N-vinylformamide composition according to claim 4, wherein the antioxidant is a phenolic compound.

8. The N-vinylformamide composition according to claim 4, which contains 95% by weight or more of N-vinylformamide.

9. The N-vinylformamide composition according to claim 4, which contains 98% by weight or more of N-vinylformamide.

10. A method of stabilizing N-vinylformamide containing formic acid, wherein the method comprises preparing N-vinylformamide containing formic acid between 1 to 250 ppm by weight based on N-vinylformamide and maintaining the content of formic acid at 1 to 250 ppm by weight based on N-vinylformamide.

11. A method of stabilizing N-vinylformamide having a formic acid content at greater than 250 ppm by weight based on N-vinylformamide, wherein the method comprises reducing the formic acid content to between 1 and 250 ppm by weight based on N-vinylformamide, and maintaining the content of formic acid between 250 ppm by weight based on N-vinylformamide.

12. The method of claims 10 or 11 wherein formic acid content is maintained by adding an antioxidant at 10 to 10,000 ppm by weight based on N-vinylformamide.

13. The method of claims 10 or 11 wherein the formic acid content is maintained by holding the N-vinylformamide under an inert environment at 30° C. or lower.

14. The method of stabilizing N-vinylformamide according to claims 10 or 11, wherein the content of formic acid is maintained between 1 and 200 ppm by weight based on N-vinylformamide.

15. The method of stabilizing N-vinylformamide according to claims 10 or 11, wherein the content of formic acid is maintained between 1 and 150 ppm by weight based on N-vinylformamide.

16. The method of stabilizing N-vinylformamide according to claims 10 or 11, wherein the method further comprises adding an antioxidant at 10 to 10,000 ppm by weight, based on N-vinylformamide.

* * * * *